United States Patent [19]

Fisler

[11] Patent Number: 5,624,404
[45] Date of Patent: Apr. 29, 1997

[54] HAND HELD PHLEBOTOMY PROTECTION DEVICE

[76] Inventor: Mitchell E. Fisler, 1030 Smyzer Rd., Townville, S.C. 29689

[21] Appl. No.: 496,400

[22] Filed: Jun. 29, 1995

[51] Int. Cl.$^6$ .................................................. A61M 5/00
[52] U.S. Cl. .......................... 604/187; 604/192; 604/63; 211/74
[58] Field of Search .................................. 604/187, 192, 604/263; 128/919, 763, 764; 206/365–367, 369, 443; 211/74

[56] References Cited

U.S. PATENT DOCUMENTS

| | | | |
|---|---|---|---|
| 4,057,148 | 11/1977 | Meyer et al. | 211/74 |
| 4,737,149 | 4/1988 | Gillilan | 604/192 |
| 4,840,618 | 6/1989 | Marvel | 604/187 |
| 4,917,672 | 4/1990 | Terndrup et al. | 604/192 |
| 4,981,476 | 1/1991 | Aichlmayr et al. | 604/192 |
| 4,982,850 | 1/1991 | Mears | 211/74 |
| 4,986,816 | 1/1991 | Steiner et al. | 604/192 |
| 5,047,019 | 9/1991 | Sincock | 604/192 |
| 5,314,413 | 5/1994 | McCowan et al. | 604/192 |
| 5,330,439 | 7/1994 | Jackson | 604/192 |

FOREIGN PATENT DOCUMENTS 1012259  12/1965  United Kingdom ............ 211/74

OTHER PUBLICATIONS

"Laboratory Safety Practices & Policies—Q–Probes Study" The College of American Pathologist 1992 pp. 1–15.

*Primary Examiner*—Vincent Millin
*Assistant Examiner*—V. Alexander
*Attorney, Agent, or Firm*—Robert R. Reed; Cort Flint

[57] ABSTRACT

The hand held phlebotomy protection device of this invention is used for safe transfer of blood from a syringe container to a plurality of test tubes held in the device by gripping the resilient handle of the device. The device is usable for any body fluid being transferred to a test tube from a syringe. The device has a shield disk with a groove and a lip to receive and stop a misguided needle before it has an opportunity to reach the hand of a user holding the device. The resilient handle has a resilient handle wall that also protects the user from a needlestick. The handle is gripped to deform the cavity cross-section holding the test tubes so the needle can be safely withdrawn to complete a safe transfer of body fluid from the syringe to a test tube.

3 Claims, 5 Drawing Sheets

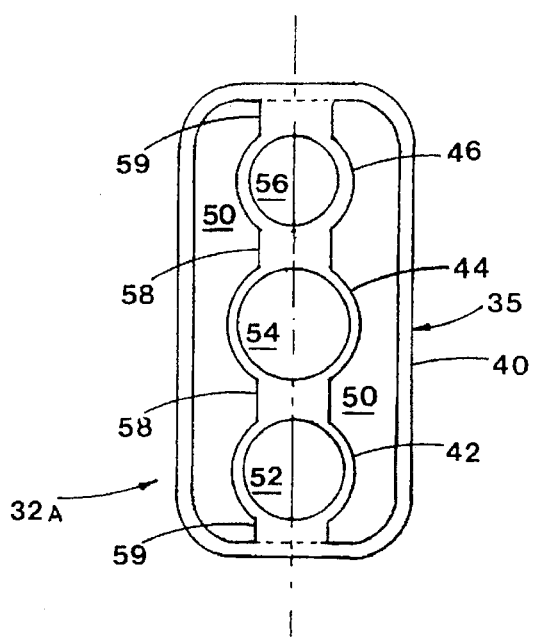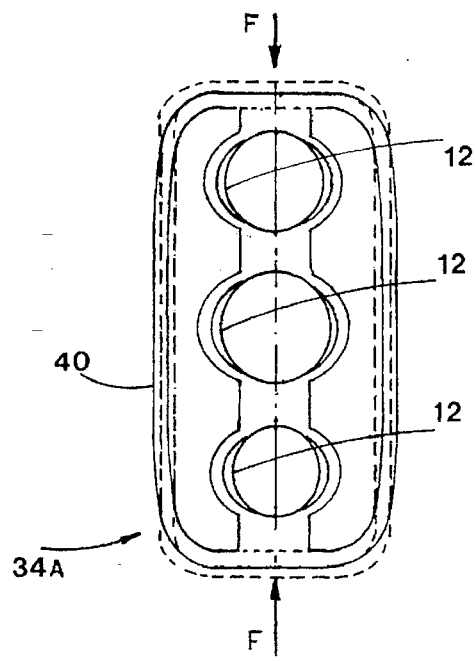
Fig. 4A  Fig. 4B
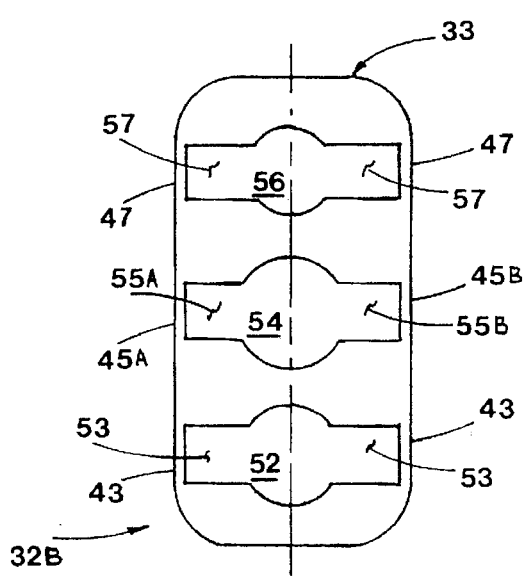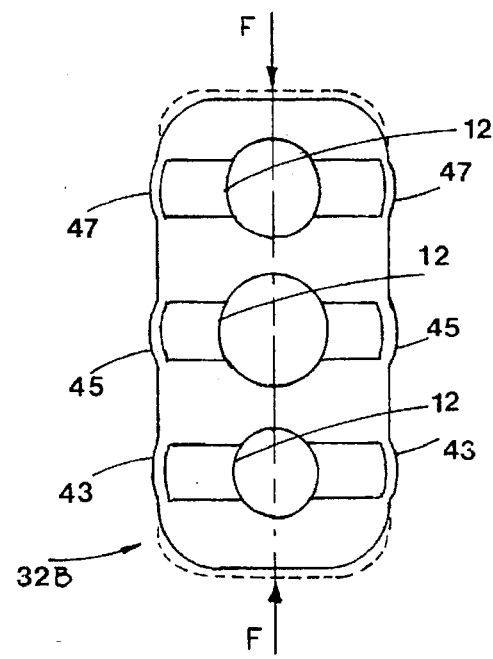
Fig. 5A  Fig. 5B

HAND HELD PHLEBOTOMY PROTECTION DEVICE

BACKGROUND OF THE INVENTION

This invention relates to a device used to assist a medical professional in the care of patients, and more particularly to protect the professional during the transfer of body fluids collected from the patient. The invention has general application and is especially suited for the transfer of blood from a syringe to test tubes as required during the tasks associated with the general area of phlebotomy.

Exposure of the health care professional or assistant to inadvertent sticking by a syringe needle in the process of transferring body fluids from the patient to other containers for laboratory evaluation is a real and constant safety problem. This is a critical problem when the transfer must occur outside the controlled conditions of the laboratory. For example, transfer of a body fluid frequently occurs in the patients room, at night, without the patient's cooperation and at the same time other tasks are being performed. Such is the case with phlebotomy and the tasks associated with transferring blood to test tubes by a phlebotomist. An accidental needlestick of the health care provider by the syringe needle provides a direct contact with the body fluids, including blood, of the patient. Such contact exposes the provider to the same infection as that of the patient and appropriate testing and treatment must be done.

A 1992 "Q-Probes" study by The College of American Pathologists showed a summary of the frequency and types of accidents and occupational injuries occurring within clinical laboratories. Data was gathered from 778 institutions in Australia, Canada and the United States. The study showed that a ratio of accidental skin puncture events to all others types of accidents and events was 1.44. That is, for every 144 skin puncture events there are only 100 other non-puncture events. In particular, the number of incidents while performing phlebotomy was 24.5 percent of all incidents. A study of high-risk employees over a 12 month period showed that the median number of needlestick or sharp injuries was six. Such data indicates a critical need to have a device to help protect the phlebotomist from needlestick injuries.

A needlestick incident is possible when the needle of the syringe becomes exposed by the health care person when collecting a body fluid sample. A number of devices have been used to keep the needle of the syringe covered prior to and after collecting the sample. In U.S. Pat. No. 4,737,149 a needle cap is held by a resilient shield during collection and transfer of the sample. This shield is only for holding the cap for covering the syringe needle. In U.S. Pat. No. 4,917,672 a sleeve is provided for the end of the syringe needle to shield the needle and keep it from dulling. This sleeve does not facilitate the transfer of body fluids to other containers. The single syringe cap holding device of U.S. Pat. No. 4,981,476 holds one small diameter cap using a U-shaped strip of a resilient sheet to wedge the cap between two apertures in the strip. A planar front plate has an upstanding lip extending around its periphery to limit an errant needle from slipping off the plate. Only a single cap can be held in this device. This is also a recapping device.

In the normal process of collecting a body fluid from a patient and processing this fluid for further analysis, a portion of the body fluid is transferred from a syringe to at least one evacuated test tube. The use of a syringe is desirable in performing phlebotomy tasks as the blood extraction rate can be controlled such that the veins of the patient do not collapse. The syringe needle must then be aligned with the test tube and the rubber stopper in the top of the tube must be penetrated by the needle. A considerable amount of skill is required to safely perform this task, especially in a dark room with a patient which may be moving. Frequently, however, this transfer is the task being performed when the needlestick incident occurs. Devices to protect the hand of the health care person in the transfer of body fluid to a single test tube are disclosed in U.S. Pat. Nos. 4,840,618 and 5,314,413.

The device disclosed in U.S. Pat. No. 4,840,618 holds a single test container and has a shield portion on the upper end of a handle. A pair of cutouts in the handle allows the contents of the container to be observed and a test tube to be held in the handle by a hand of an operator when the syringe needle is being extracted from the test tube. The shield has a ridge on the peripheral edge of the shield should the needle attempt to slide off the edge. This single test tube device does not provide for multiple test tubes to be sequentially filled from one syringe of body fluid.

The need to have a device to hold different size test tubes is recognized in U.S. Pat. No. 5,314,413. A number of test tube or vial openings are rotatably disposed on a shield plate having a deflector ridge. A handle is provided to support the shield plate and a thumb and forefingers are used to support the vial when being filled and when pulling the needle from the vial. A pinching type grip is required to support the vial using this vial handler tool and only one vial can be filled before an interchange of vials in the tool.

With a single collection of a body fluid from the patient a number of test tubes can be partially filled. The purpose of multiple tubes is that there are certain tubes used only by the chemistry lab, other tubes are used by the hematology lab, additional tubes are used by the blood bank, and so on. The ordering physician usually requests a variety of tests that require the use of 3 to 4 different tubes at one time. These tubes vary in size from about 1.2 millimeter in diameter to about 1.6 millimeter in diameter depending on the type of test and the laboratory doing the test.

Devices that hold a number of test tubes are disclosed in U.S. Pat. Nos. 4,982,850 and 5,330,439. In U.S. Pat. No. 4,982,850 five vertical shafts for housing vials are illustrated. An oval base and a overlying horizontal shield having an outer edge help support the device on a table and protect the hand of the health-care professional. The user can press each vial against the back of a respective shaft through a frontal slot in each shaft to hold the vials steady while inserting and removing the syringe needle. It is necessary to have a vial in each shaft to prevent an errant needle from entering a shaft and penetrating the hand of the user. Only certain vials can be held at any one time by the thumb of the user when transporting the holder.

The device of U.S. Pat. No. 5,330,439 has a detachable safety overshield with a projecting peripheral rim to catch the depositing needle and keep it on the face of the overshield. A collection tube retainer having one or more tubes therein is held in the hand of the user. The tube retainer does not protect against tube breakage. The safety overshield is attachable to the top of the tube retainer and covers the stopper of the collection tubes to hold the tubes in place during insertion and removal of the syringe needle. Once again, there is only limited protection for the hand of the user if all holes in the overshield are not filled with collection tubes.

An unsatisfied need remains to have a hand held device that holds one or a number of test tubes and fully protects the hand of the health-care professional during the transfer of syringe collected body fluid to the test tubes. The device needs to be economical to purchase, easy to use and assists the user in its proper operation.

Accordingly, an object of the present invention is to provide the health-care professional with a hand held device to make safe the transfer of body fluids from a syringe to a plurality of test tubes. This device should be useful in a laboratory as well as during direct care of the patient in the patient's room.

Another object of the present invention is to reduce the risk to exposure to injury and illness from direct contact with blood and other body fluids from a patient under the care of a care provider. Direct exposure from a needlestick injury is of a specific concern with the direct object of reducing the large percentage of such incidents.

Yet another object of the present invention is to provide a light weight hand held device which is easy to use to reduce the number of needlestick injuries to the high risk phlebotomist collecting many blood samples each work day. The device is to be designed to protected the hand of the user when a syringe needle is misaligned or misguided.

In still another object the hand held device is made to be used when filling a number of test tubes at one time from a single syringe. The device used in the process of collecting samples from a patient is to accommodate the physician ordering a variety of tests that require a variety of test tube sizes.

SUMMARY OF THE INVENTION

The above objectives are accomplished according to the present invention by a hand held protection device having a shield disk supported by a resilient handle that holds the test tubes within adjustable cavities within the handle. The shield disk has a continuous groove and a continuous lip at its top surface to guard the hand of the user from an errant syringe needle. The device is especially useful by the phlebotomist collecting blood from a patient and transferring the blood to test tubes for further laboratory analysis.

In general, the device of this invention is held in the hand of an operator or user for safe transfer of any body fluid from a syringe to a plurality of test tubes. In particular, the device comprises a resilient handle for being held in the hand having a plurality of adjustable cavities that are generally continuous over the full length of each test tube of the plurality of test tubes placed within a respective cavity. The device also comprises a continuous resilient handle wall to protect the hand from contact with a needle of the syringe in the process of safe transfer of the body fluid to each test tube. The device further comprises a shield disk extending laterally from the upper end of the handle to a distance such that a clenched fist of the hand about the handle is shielded from sustaining a puncture from a needle of the syringe. A plurality of cutouts within the disk communicate with the plurality of cavities in the handle. The adjustable cavities having an initial cross-section for receiving the test tubes and a deformed cross-section being deformed relative to the initial cross-section for gripping the test tubes to prevent removal of the test tube when a sufficient gripping force is imparted to the resilient handle.

As another embodiment, the shield disk further has a top surface for supporting a stopper of each one of the test tubes above the disk to help facilitate the safe transfer of the body fluid to the plurality of test tubes. The top surface has a color with a shade that provides a contrast with another color of the stoppers of the plurality of test tubes. In addition, a continuous protective groove is included in the top surface of the disk to enclose the cutouts and to receive and stop an errant needle of the syringe which has been forcibly misaligned with a respective stopper of a respective test tube. Finally, a continuous protective lip having an upstanding leg may be included adjacent an outer edge of the disk to also receive and stop an errant needle of the syringe.

Further embodiments of the resilient handle include a plurality of resilient tubular shafts having a generally continuous hollow internal cavity forming the plurality of adjustable cavities lengthwise within the handle. A plurality relatively rigid web members are positioned between the tubular shafts as well as between the resilient handle wall and respective tubular shafts such that the gripping action decreases the initial cross-section of each adjustable cavity in one direction to achieve the deformed cross section.

The invention has functional utility as defined by a method for transferring a body fluid from a syringe to a plurality of test tubes. The method has a first step of providing a resilient handle having a plurality of adjustable cavities with an initial cross-sectional shape. In a second step, a shield disk is provided that extends laterally from an upper end of the handle for protecting a clenched fist of a hand of an operator, the hand being placed around the handle and the disk having a plurality of cutouts that communicate with the cavities. A third step includes protecting the plurality of test tubes by placing the tubes within respective cavities of the handle such that a stopper of each test tube of the plurality of test tubes projects above a top surface of the disk and the cavity generally extends the full length of each test tube. The fourth step of the method further includes gripping the handle for supporting the disk to shield the hand from sustaining a needlestick from a needle of the syringe. In the fifth step the stopper of a respective test tube is penetrated with the needle an body fluid is transferred into the respective tube. A sixth step includes adjusting the initial cavity cross-section of the plurality of cavities by further gripping the handle with the hand to achieve a deformed cavity cross-section. In the seventh step, the method includes holding the plurality of test tubes within the plurality of cavities by the adjustment step (f) to bring contact between a portion of the interior surface of a single cavity having the respective test tube therein and a portion of the outer surface of the respective test tube. In yet another eighth step the method includes pulling the needle of the syringe from the stopper of the respective test tube to complete the transfer of the body fluid from the syringe to the respective test tube. The final ninth step includes repeating steps (e) through (h) until all test tubes of the plurality of test tubes contain a predetermined amount of the body fluid.

DESCRIPTION OF THE DRAWINGS

The construction designed to carry out the invention will hereinafter be described, together with other features thereof.

The invention will be more readily understood from a reading of the following specification and by reference to the accompanying drawings forming a part thereof, wherein an example of the invention is shown and wherein:

FIG. 4A is a cross-sectional plan view of the handle of the preferred device of this invention along line 4—4 in FIG. 3;

FIG. 4B is a cross sectional plan view of the handle of the preferred device of this invention cut along line 4—4 in FIG. 3, showing the handle being deformed by a gripping force;

FIG. 5A is a cross-sectional plan view of another handle embodiment of the device of this invention;

FIG. 5B is a cross-sectional view of the other handle of the device showing the other handle being deformed by a gripping force.

DESCRIPTION OF A PREFERRED EMBODIMENT

Referring now in general to the drawings, the invention is described in general terms. The safe transfer of a body fluid to a plurality of test tubes after collecting the body fluid in a syringe is accomplished by the hand held device of this invention. The hand held device has a shield disk to protect the clenched fist as it grips the resilient handle of the device. The resilient handle is gripped in the hand to hold the test tubes in place for penetration and removal of a syringe needle. The test tubes are also held in place by gripping the resilient handle to allow the test tubes to be inverted while mixing the body fluid deposited into the test tubes with other chemicals predisposed in the test tubes. Details of the device, including its structural and functional features, are disclosed in the following detailed discussions of the figures.

Figure 1:
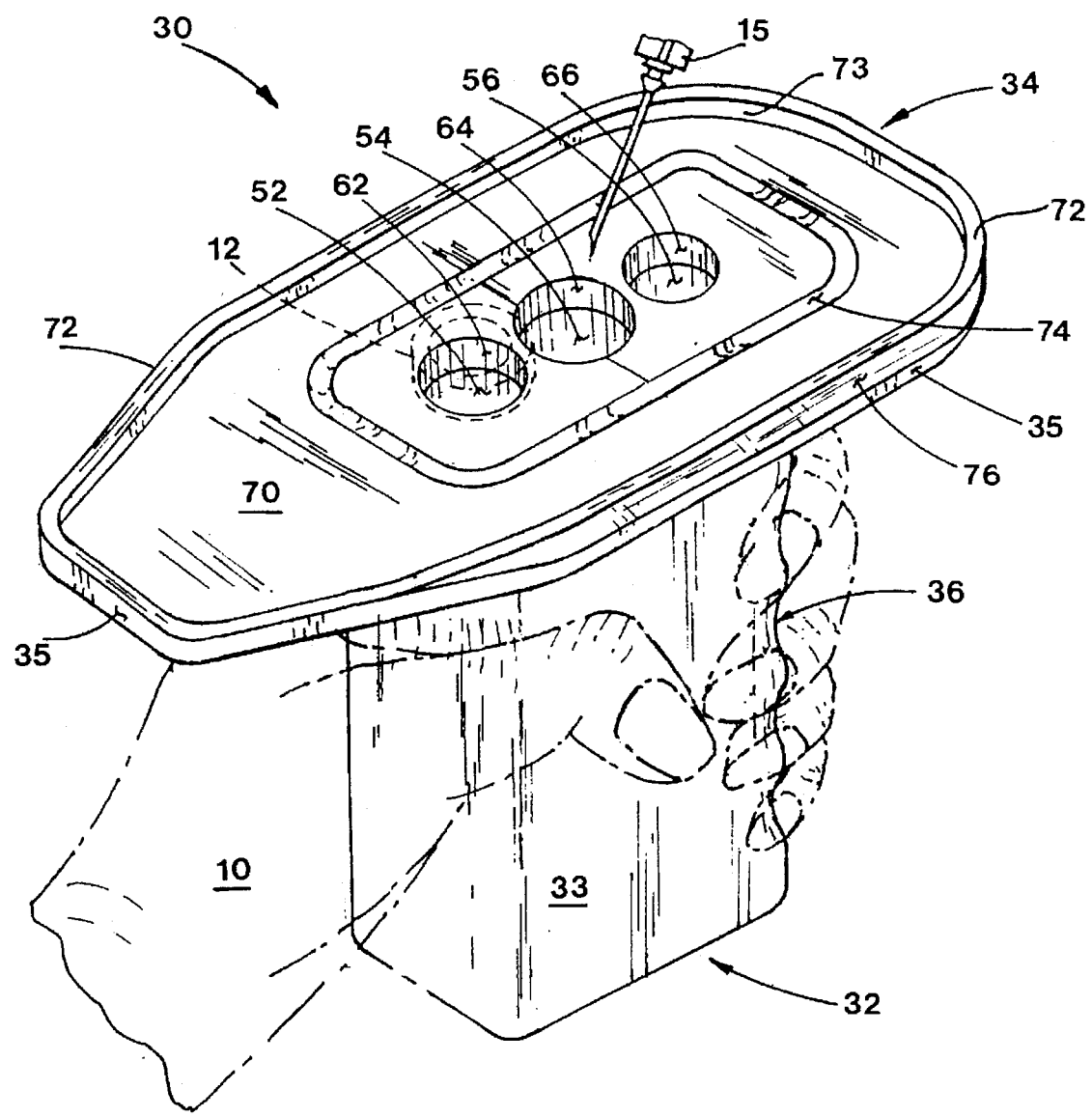
FIG. 1 is a perspective view of a preferred device of this invention being held by the user prior to test tubes being inserted therein.

The device 30 being held in a hand 10 of a health-care provider is illustrated in FIG. 1. A shield disk 34 is positioned above the clinched fist of the hand 10 of the health-care provider, and is shaped to protect the fingers and the hand to a location near the wrist. The resilient handle 32 supports the disk 34 and has a pistol grip portion 36 for correct gripping of the handle and positioning of the shield disk above the hand. Three adjustable cavities 52, 54 and 56 in the resilient handle 32 are positioned to each receive a test tube. The number of test tubes can be more or less within the scope of this invention. However, the preferred three test tubes provide a handle size that can be easily held and gripped by any individual user. Test tubes of different size are provided for by having an internal cavity cross-section to correspond with each different size test tubes. Cutouts 62, 64 and 66 in the disk 34 communicate with the cavities in the handle 32. A snug fit is provided within each cavity to hold a respective test tube in an upright position within the handle and to bring each test tube adjacent to structure within the handle 32.

Figure 6:
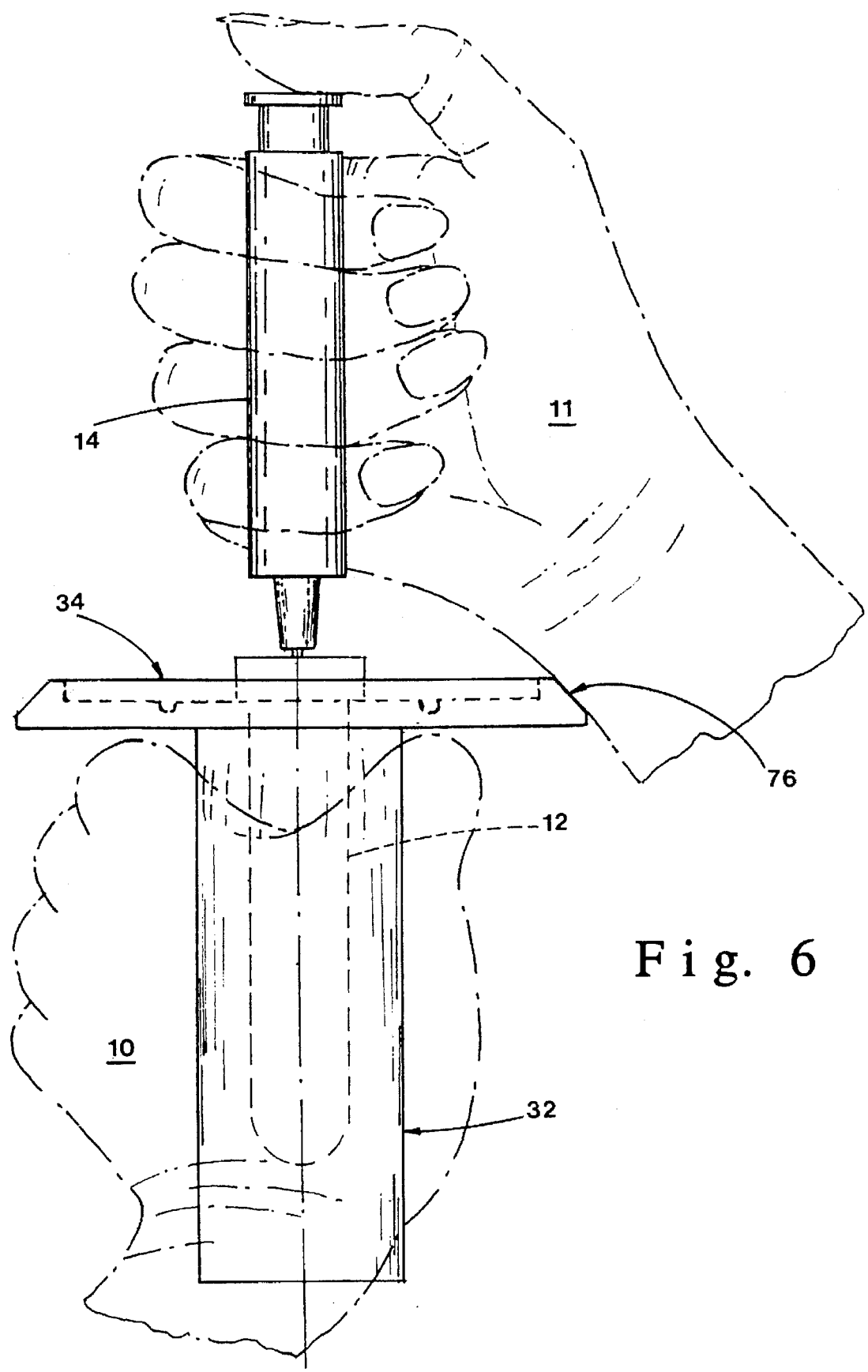
FIG. 6 is an elevation view of the preferred device of this invention showing another hand of the user in a hand rest position on the device.

A syringe needle 15 of FIG. 1 is shown to be misaligned with a stopper of a test tube 12 as illustrated by the dashed lines. This errant needle is a common cause of injuries that occur with the safe transfer of the body fluid from a syringe to a test tube. The errant syringe needle may strike a top surface 70 of the shield disk 34 or it may enter one of the unfilled cavities 54 and 56. The hand is protected from this errant needle by stopping the needle on the top surface and by the handle providing a continuous protective handle wall. A continuous protective groove 74 is provided in the top surface to receive and stop the needle. This continuous groove is placed to enclose the cutouts in the shield disk. A continuous protective lip 72 adjacent an outer edge 35 of the disk is provided to also receive and stop the errant needle. The lip has an upstanding leg 73 to provide a vertical surface to stop the errant needle. To further assist the health-care provider in obtaining a proper alignment with said respective test tube, a handrest 76 being a flat surface area along at least a portion of the outer edge of the disk is provided. Two such handrests may be provided for both right handed and left handed users; being one on each lateral side of the disk as held by the user in the opposite hand. The illustration of FIG. 1 shows the device held in the left hand and a handrest is provided for the right hand as illustrated in FIG. 6.

Figure 2:
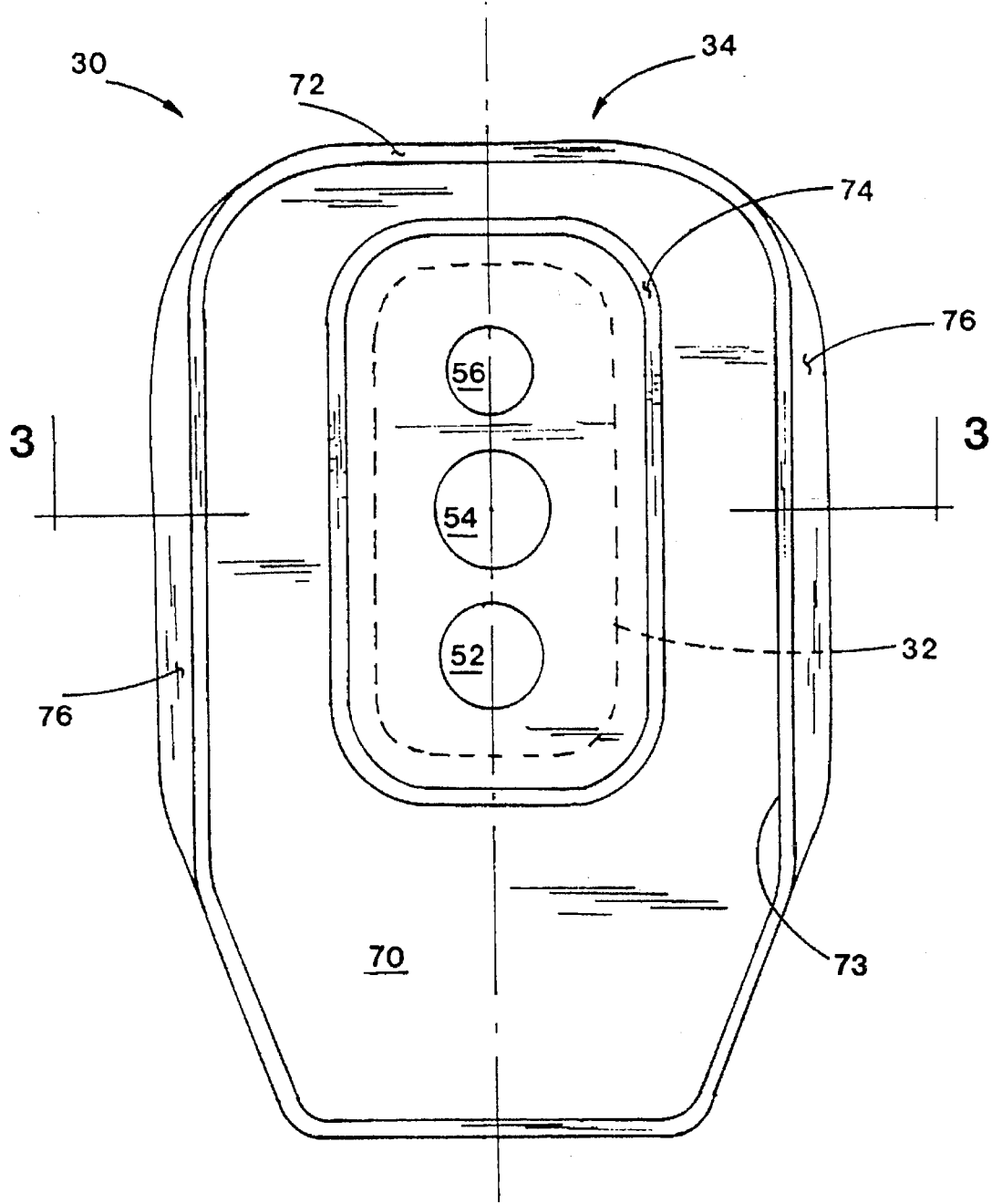
FIG. 2 is a top plan view of the preferred device of this invention showing three cylindrical cavities.

Details of the a symmetrically shaped shield disk 34 are illustrated in FIG. 2. The device 30 of this preferred embodiment can be held either with the left or the right hand. The three adjustable cavities 52, 54 and 56 are positioned within the resilient handle 32 below the disk shown. The cavities are adjustable by deforming the handle. Two handrests 76 are provided, being one on each lateral side of the shield disk 34. The top surface 70 of the disk has both a continuous groove 74 and a continuous upstanding leg 73 provided to receive and stop a forcibly misaligned syringe needle. Test tubes of an appropriate size are placed within each cavity.

Figure 3:
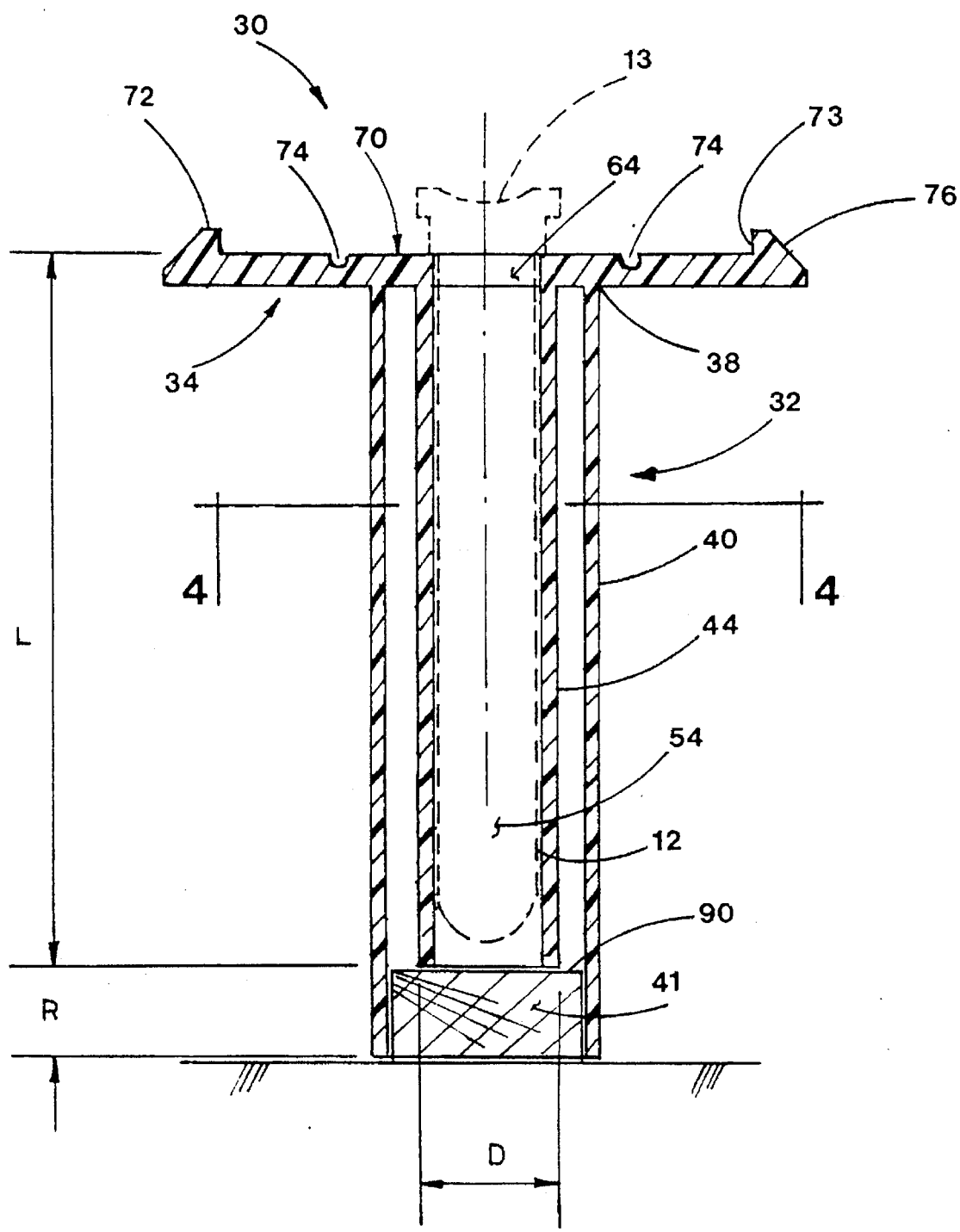
FIG. 3 is an cross-sectional elevation view of a handle of the preferred device of this invention along line 3—3 in FIG. 2.

Test tubes commonly used in the medical laboratory and specified by the health-care professional vary in their outside diameter over a range of values of about 1.2 centimeters to about 1.6 centimeters. The illustration of FIG. 3 shows a cross-section of the device 30 viewed along line 3—3 in FIG. 2. A typical test tube 12 is placed within the adjustable cavity 54 in the resilient handle 32. A stopper 13 of the test tube 12 rests on the top surface 70 of the disk 34 which supports the stopper when it is being penetrated by a syringe needle. A resilient handle wall 40 and/or a tubular shaft 44 protects the hand if a syringe needle should penetrate the cavity 54. The resilient handle wall encloses the shafts and both are continuous or uninterrupted, as illustrated in FIGS. 3, 4 and 6. The protective groove 74 and the protective lip 72 keep a forcibly misguided needle contained above the top surface 70 of the disk 34. The length L of the cavity plus the cutout 64 in the disk is adequate to extend at least the full length of any respective test tube inserted in a respective cavity. The initial cavity cross-sectional diameter D is only large enough to provide a snug fit with the test tube 12. The initial cavity cross-sectional diameter D should be less than one millimeter larger than an outside diameter of a respective test tube for which each cavity is predetermined to accommodate.

A handle cutout 41 with a recess length R is preferably provided in the lower end of the handle 32 to allow the device to be supported in an upright position on a table support attachment 90 when not in use, or when test tubes are be placed in or removed from the cavities. The recess and table support attachment will allow the syringe to be continuously held in the other hand and continuous control of the syringe needle location is improved.

The resilient handle 32 of the hand held device 30 has a material and structural configuration being deformable and capable of holding the test tubes within the device during safe transfer of a body fluid, such as blood, from a syringe container to the test tubes. It is essential that the resilient handle 32 be deformed by the user gripping the resilient handle to change the initial cavity cross-section and thereby to provide a smaller deformed cavity cross-sectional dimension in one direction to bring contact between the internal surface of each adjustable cavity and the exterior surface of each test tube. The handle structural configuration illustrated in the cross-sections of FIGS. 4A and 4B show the preferred handle 32A of this invention. A continuous resilient handle wall 40 provides protection for the hand and resilient tubular shafts 42, 44 and 46 form adjustable cavities 52, 54 and 56 within the handle. Substantially rigid web members 58 and 59 extend between tubular shafts and between a tubular shaft and an adjacent handle wall respectively. A volume 50 void of any material is provided between the handle wall 40 and the tubular shafts with the web members. The effect of gripping the handle 30 provides a force F that deforms external handle wall 40 of the resilient handle 32A as illustrated in FIG. 4B. The initial cavity cross-section of each adjustable cavity is decreased until a deformed cross-section is achieved sufficient for the internal surface area of each adjustable cavity to contact an external surface of each test tube 12. A snug fit of each test tube within a respective cavity is provided by the initial cross-section.

In another embodiment a resilient handle 32B of the device is made relatively solid, as illustrated in FIGS. 5A and 5B. A pair of notches projecting from each adjustable cavity 52, 54 and 56 to an end near the external surface 33 of the handle forms a pair of deformable handle wall sections adjacent each cavity. For example, deformable wall sections 45A and 45B are formed adjacent the adjustable cavity 54 by the pair of notches 55A and 55B. Similar notches 53 and 57 form similar wall sections 43 and 47 for the adjustable cavities 52 and 56. Gripping the resilient handle 30 provides a force F that deforms the handle and deflects the wall sections 43, 45 and 47. This deformation reduces the initial cavity cross-section to form a smaller deformed cavity cross-section in one direction sufficient to make an internal surface of each cavity contact an external surface of each test tube and hold the test tubes within the cavities, as illustrated in FIG. 5B. This is necessary to extract the needle from the stopper. The needle cannot be withdrawn from the stopper without gripping the handle to hold the test tube.

The material used for the resilient handle is critical for holding each test tube within a respective cavity. The resilient handle 32 is made of a plastic material that is generally non-penetratable with a needle of a standard syringe used in the medical profession to collect body fluids. The plastic material must be resilient and deformable when gripped by a hand of the user. The plastic material is to have a dry static coefficient of friction of at least 0.50 when in contact with a glass surface. The dry static friction should be sufficient to hold the test tubes within the cavities by the gripping force of a health-care provider on the resilient handle 30. The shield disk 34 can be of the same material as the resilient handle for ease in manufacturing the device as one single unit. A separate material being of a different and more rigid plastic can be used for the disk within the scope of this invention. A number of plastic materials used in the industry are sufficient for the materials of this device.

The illustration of FIG. 6 shows the health-care provider with the resilient handle 32 held in the left hand 10 and the syringe 14 held in the right hand 11. The handrest 76 provides a flat surface or positioning the syringe above the test tube 12. The improved device of this invention provides many advantages over other devices in the industry. These include but are not limited to the following:

a) The device holds more than one test tube;

b) The test tubes are gripped and held within the device;

c) The use of a resilient material allows the handle to be deformed to hold the test tubes;

d) The device is light weight and easy to manufacture;

e) A groove on the top surface helps to stop an errant needle;

f) The top surface is made a color in contrast to the various colors of stoppers of test tubes;

g) The test tubes can all be held in an inverted position with one hand for mixing fluids in the tubes;

h) A completely continuous resilient wall of the handle protects the test tubes on all sides from being broken and at the same time protects the users hand; and i) A pistol grip handle configuration helps the user position the disk and grip the handle.

While a preferred embodiment of the invention has been described using specific terms, such description is for illustrative purposes only, and it is to be understood that changes and variations may be made without departing from the spirit or scope of the following claims.

What is claimed is:

1. A device held in the hand of an operator for a safe transfer of a body fluid from a syringe to a plurality of test tubes, said device comprising:

a resilient handle for being held in the hand having a plurality of adjustable tubular shafts with walls that are generally uninterrupted over the full length of said test tubes placed within a respective tubular shaft, said handle having an upper end and a lower end;

an uninterrupted resilient exterior handle wall included in said handle and enclosing said shafts between said upper and lower ends for being gripped by said operator's hand and to protect said hand from contact with a needle of said syringe in the process of said safe transfer of said body fluid to said each test tube;

a shield disk extending laterally from said handle near said upper end to a lateral distance such that a clenched fist of said hand about said handle wall is shielded from sustaining a puncture from a needle of said syringe;

a plurality of cutouts within said disk to communicate with said plurality of tubular shafts in said handle; and each one of said adjustable tubular shafts having an initial cross-section for receiving a respective test tube, and said adjustable tubular shaft having a deformed position in which said initial cross-section is deformed when a sufficient gripping force is imparted to said resilient handle wall by said operator's hand for gripping said test tube to prevent removal.

2. The device set forth in claim 1, including a handrest having a beveled, smooth and flat surface area along at least a portion of an outer edge of said disk for said operator to align and rest a portion of a surface area of another hand on said flat surface area, said other hand having said syringe therein.

3. The device in claim 1, wherein said plurality of resilient tubular shafts each have a generally continuous hollow internal cavity forming a plurality of adjustable cavities lengthwise within said resilient handle, wherein each cavity forms a generally snug fit with a respective tube when said tubular shafts are deformed.

* * * * *